(12) United States Patent
Sase et al.

(10) Patent No.: US 9,901,357 B2
(45) Date of Patent: Feb. 27, 2018

(54) BODY CAVITY FOREIGN MATTER CAPTURE INSTRUMENT

(71) Applicant: PIOLAX MEDICAL DEVICES, INC., Yokohama-shi (JP)

(72) Inventors: Risa Sase, Yokohama (JP); Satoshi Yoshita, Yokohama (JP); Hirofumi Kawamoto, Okayama (JP)

(73) Assignee: PIOLAX MEDICAL DEVICES, INC., Yokohama-Shi, Kanagawa (JP)

( * ) Notice: Subject to any disclaimer, the term of this patent is extended or adjusted under 35 U.S.C. 154(b) by 161 days.

(21) Appl. No.: 14/901,515

(22) PCT Filed: Jul. 2, 2014

(86) PCT No.: PCT/JP2014/067636
§ 371 (c)(1),
(2) Date: Dec. 28, 2015

(87) PCT Pub. No.: WO2015/002225
PCT Pub. Date: Jan. 8, 2015

(65) Prior Publication Data
US 2016/0151080 A1 Jun. 2, 2016

(30) Foreign Application Priority Data
Jul. 2, 2013 (JP) ................................. 2013-138775

(51) Int. Cl.
*A61B 17/22* (2006.01)
*A61B 17/221* (2006.01)

(52) U.S. Cl.
CPC .... *A61B 17/221* (2013.01); *A61B 2017/2212* (2013.01)

(58) Field of Classification Search
CPC .......... A61B 17/221; A61B 2017/2212; A61B 17/32056
See application file for complete search history.

(56) References Cited

U.S. PATENT DOCUMENTS

| 4,347,846 A | 9/1982 | Dormia |
| 6,174,318 B1 * | 1/2001 | Bates .................. A61B 17/221 |
| | | 606/113 |

(Continued)

FOREIGN PATENT DOCUMENTS

| JP | 56-95041 A | 8/1981 |
| JP | H09-019438 A | 1/1997 |

(Continued)

OTHER PUBLICATIONS

International Search Report (ISR) (PCT Form PCT/ISA/210), in PCT/JP2014/067636, dated Jul. 29, 2014.
Extended European Search Report dated Nov. 22, 2016.

*Primary Examiner* — Ashley Fishback
(74) *Attorney, Agent, or Firm* — McGinn IP Law Group, PLLC

(57) ABSTRACT

The foreign matter capture instrument includes: a first manipulation wire; framework wire materials, the base end parts being coupled to a leading end part of the first manipulation wire, and the leading end parts being respectively bundled together; and a second manipulation wire which is coupled to the leading end parts of the framework wire materials, separates from the first manipulation wire extending toward the base end side of the first manipulation wire. By moving the first manipulation wire toward the leading end side relative to the second manipulation wire, the framework wire materials expand and configure a basket, and by further relatively moving the first manipulation wire toward the leading end side, the basket becomes shallower.

6 Claims, 25 Drawing Sheets

(56) References Cited

U.S. PATENT DOCUMENTS

| | | |
|---|---|---|
| 2003/0109889 A1 | 6/2003 | Mercereau et al. |
| 2008/0177276 A1 | 7/2008 | Teague et al. |
| 2009/0024139 A1 | 1/2009 | Saleh |
| 2009/0105723 A1 | 4/2009 | Dillinger |
| 2011/0160741 A1 | 6/2011 | Asano et al. |
| 2014/0012283 A1* | 1/2014 | Yasuda ................ A61B 17/221 606/127 |

FOREIGN PATENT DOCUMENTS

| | | |
|---|---|---|
| JP | 2000-504595 A | 4/2000 |
| JP | 2001-517527 A | 10/2001 |
| JP | 2003-530944 A | 10/2003 |
| JP | 2005-511192 A | 4/2005 |
| WO | WO 97/27808 A1 | 8/1997 |
| WO | WO 99/16364 A1 | 4/1999 |
| WO | WO 99/16365 A1 | 4/1999 |
| WO | WO 01/80748 A2 | 11/2001 |
| WO | WO 03/049625 A1 | 6/2003 |
| WO | WO 03/061483 A3 | 7/2003 |
| WO | WO 2009/031338 A1 | 3/2009 |
| WO | WO 2009/055098 A1 | 4/2009 |
| WO | WO 2009/150920 A1 | 12/2009 |

* cited by examiner

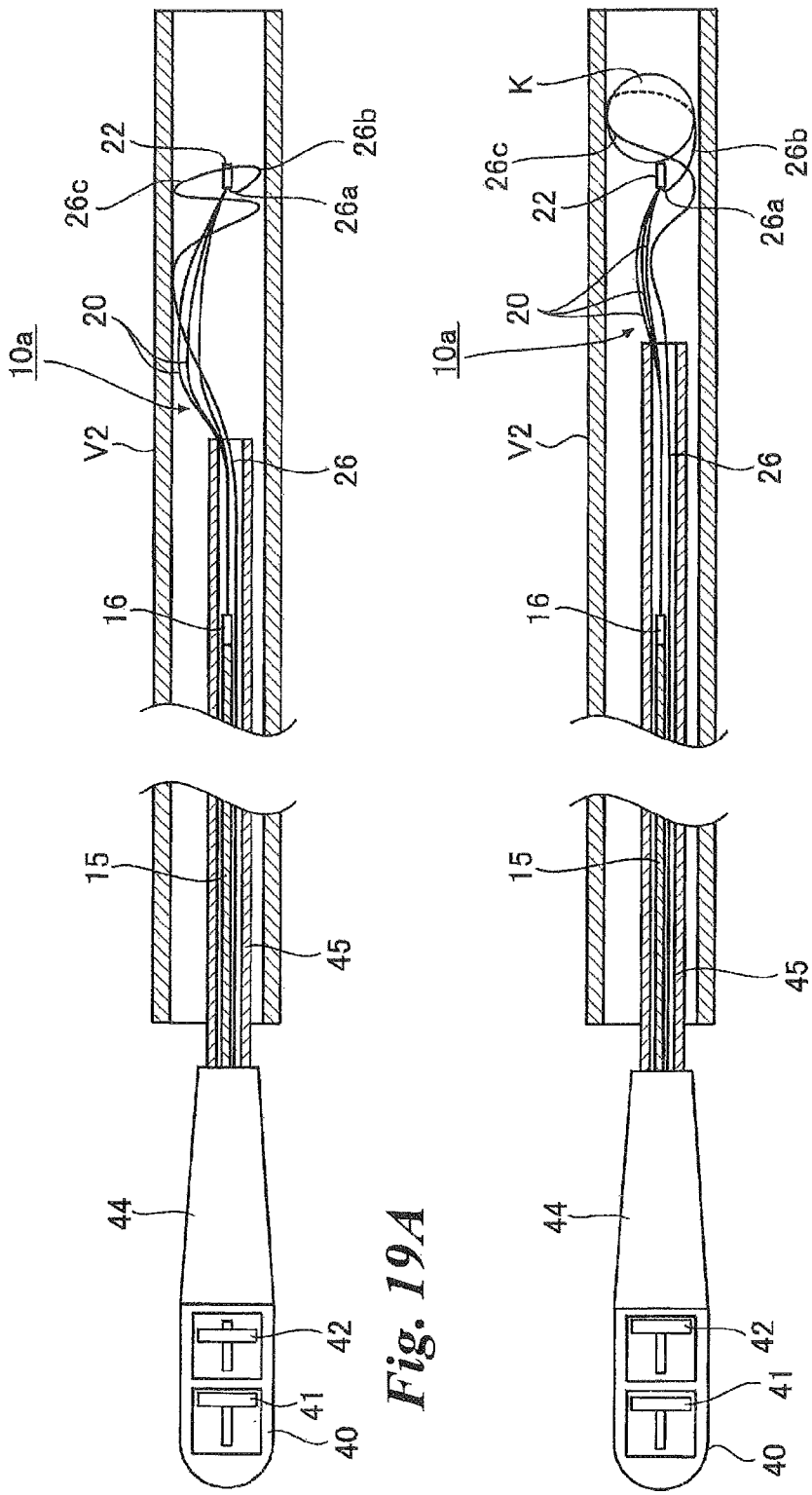

BODY CAVITY FOREIGN MATTER CAPTURE INSTRUMENT

TECHNICAL FIELD

The present invention relates to a body-cavity foreign object capturing device for capturing a foreign object which is produced in a body cavity of the human body, such as a tubular organ.

BACKGROUND ART

A foreign object such as a gallstone, a pancreatic stone, or a thrombus is sometimes produced in a tubular organ such as the bile duct, the pancreatic duct, the ureter, a blood vessel, or another body cavity of the human body. Therefore, an operation of capturing such a foreign object and removing it from a body cavity is performed.

For example, Patent Literature 1 discloses a treatment tool for a tubular organ, including: a tube; a wire which is inserted through the tube; a basket which is formed into a tubular shape by knitting metal wire members, and in which base end portions thereof are bundled together and coupled to a distal end portion of the tube, and distal end portions are bundled and coupled to a distal end portion of the wire; and a handle portion which holds a base end portion of the tube, and which holds a base end portion of the wire in a manner that the wire is movable relative to the tube.

The basket has an approximate spindle shape in which the ends of the tubular member are reduced in diameter into a tapered shape. In the basket, the wire is placed in the middle, the distal end side has a mesh shape formed by plural metal wire members, the plural metal wire members are bundled together to form plural bundled portions in the base end side, and openings are formed between them.

In an actual use of the treatment tool, the handle portion is operated to pull the wire toward the proximal side to expand the diameter of the basket, a foreign object is received through the opening to be captured, the basket is then moved to the duodenum or the like, the handle portion is operated in the position to push and pull the wire, thereby expanding and contracting the diameter of the basket, and the foreign object is discharged through the opening of the basket.

CITATION LIST

Patent Literature

Patent Literature 1
WO-2009-150920-A

SUMMARY OF INVENTION

Problem to be Solved by Invention

In the case of the treatment tool of Patent Literature 1, however, the wire is placed in the center of the basket. When the diameter of the basket is expanded for receiving a foreign object through the opening, therefore, the wire serves as an obstacle, and a foreign object which is relatively large, such as a gallstone is sometimes hardly captured.

In a tubular organ such as the bile duct, plural stones are sometimes produced in a line along the path of the tubular organ (referred to as stacked stones or the like). In this case, with a structure for capturing a foreign object by expanding the diameter of a basket as employed in the above-described treatment tool, the diameter of the basket is contracted, the basket is passed between the stones and the tubular organ, and placed in front of the leading stone, and then the diameter of the basket is expanded and pulled to the proximal side, thereby capturing the plural stones. However, it is not easy to collectively capture plural relatively-large stones. The stones may get stuck in the middle of the tubular organ, and may not be taken out.

An object of the invention is to provide a body-cavity foreign object capturing device which can easily capture even a relatively-large foreign object.

Solution to Problem

In order to attain the object, the present invention provides a body-cavity foreign object capturing device including:
a first operation wire;
plural framework wire members, base end portions of which are coupled to a distal end portion of the first operation wire, and distal end portions of which are bundled together; and
a second operation wire which is coupled to the distal end portions of the plural framework wire members, which extends toward a base end of the first operation wire while being separated from the first operation wire, and which is operable independently from the first operation wire.

There may be preferably provided,
the body-cavity foreign object capturing device,
wherein the second operation wire is caused to have a curved shape as a free-state initial shape as viewed from an axial distal end side.

There may be preferably provided,
the body-cavity foreign object capturing device,
wherein the second operation wire is configured to expand in an outer radial direction by moving the second operation wire relative to the first operation wire toward the distal end, and to move to the distal end side with respect to a coupling portion between the distal ends of the plural framework wire members and the distal end of the second operation wire by further relatively moving the second operation wire toward the distal end.

There may be preferably provided,
the body-cavity foreign object capturing device,
wherein the framework wire members are configured to expand to form a basket by moving the first operation wire relative to the second operation wire toward the distal end, and a depth of the basket is reduced by further relatively moving the first operation wire toward the distal end.

There may be preferably provided,
the body-cavity foreign object capturing device,
wherein a resin membrane is disposed in a portion of the basket,
wherein the portion ranging from a coupling portion between distal end portions of the plural framework wire members and a distal end portion of the second operation wire, to a portion where a diameter of the basket is maximally expanded.

There may be preferably provided,
the body-cavity foreign object capturing device,
wherein the plural framework wire members are placed at predetermined intervals along a circumferential direction thereof in a state where the diameter of the basket is expanded,
wherein the second operation wire is configured by a single wire, and placed in a position circumferentially opposed to a portion where the plural framework wire members are placed in the state where the diameter of the basket is expanded, and wherein an interval between the second operation wire and one of the framework wire members which is closest to the second operation wire is wider than intervals among the plural framework wire members.

Advantageous Effects of Invention

According to the invention, the second operation wire is caused to tangle with a foreign object in a body cavity by moving the second operation wire relative to the first operation wire toward the distal end, and the foreign object can be captured by interposing the foreign object between the plural framework wire members which are coupled to the first operation wire, and the second operation wire, and then taken out from the body cavity.

BRIEF DESCRIPTION OF DRAWINGS

FIG. 17A is a diagram of a case where the second operation wire is in the free state. FIG. 17B is a diagram in a state where the second operation wire is moved toward the distal end.

FIG. 18A is a side view diagram of a case where the second operation wire is moved toward the distal end in the state of FIG. 14. FIG. 18B is a side view diagram of a case where the second operation wire is moved toward the distal end in the state of FIG. 18A.

FIGS. 19A and 19B show an operation of the foreign object capturing device. FIG. 19A is a side view diagram of a case where the second operation wire is moved toward the distal end in the state of FIG. 18A. FIG. 19B is a side view diagram of a case where the second operation wire is moved toward the distal end in the state of FIG. 19A.

FIG. 21A is a diagram of a case where the second operation wire is in the free state. FIG. 21B is a diagram of a state where the second operation wire is moved toward the distal end.

FIG. 22A is a diagram of a case where the second operation wire is in the free state. FIG. 22B is a diagram of a state where the second operation wire is moved toward the distal end.

DESCRIPTION OF EMBODDIMENTS

Hereinafter, an embodiment of a body-cavity foreign object capturing device according to the invention will be described with reference to FIGS. 1 to 13.

Figure 1:
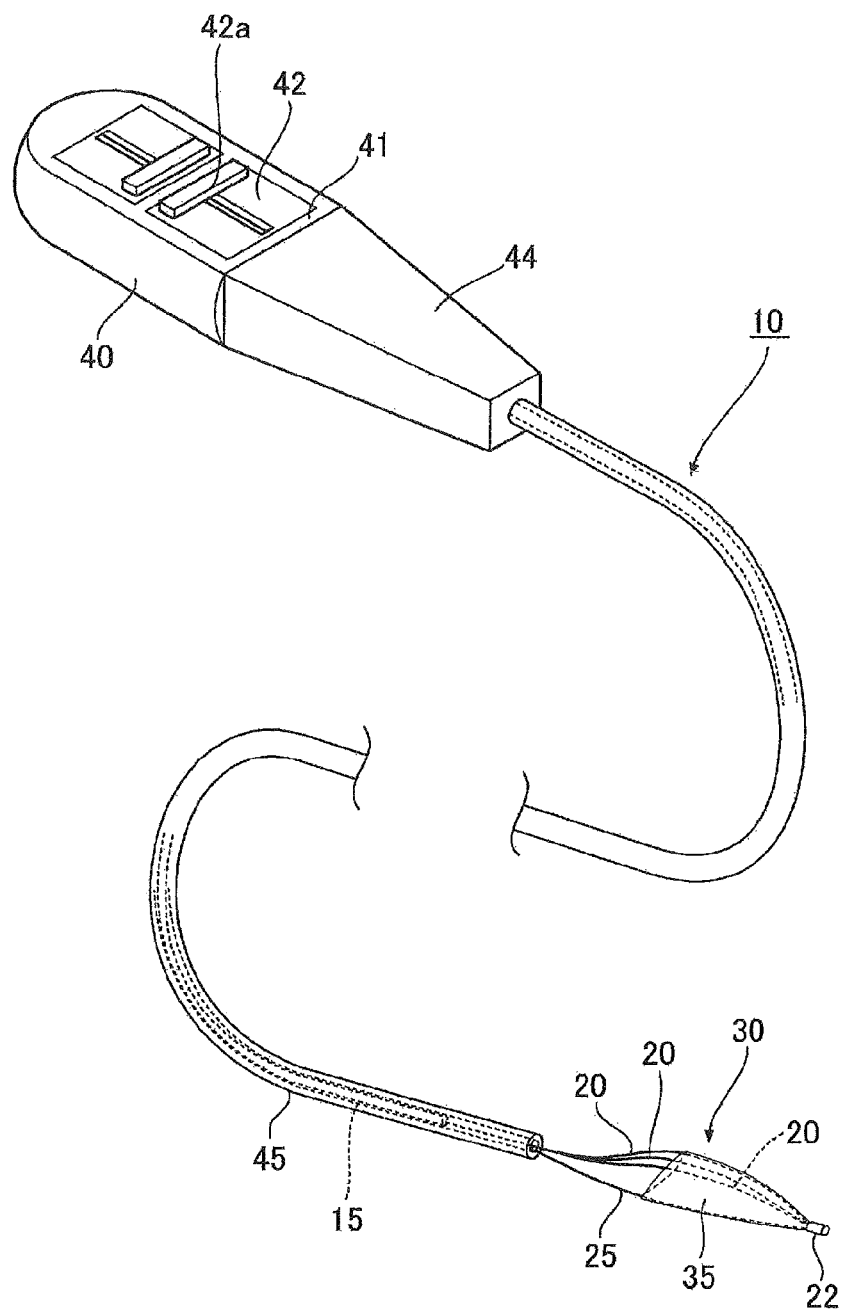
FIG. 1 is a perspective view showing an embodiment of the body-cavity foreign object capturing device according to the invention.
Figure 2:
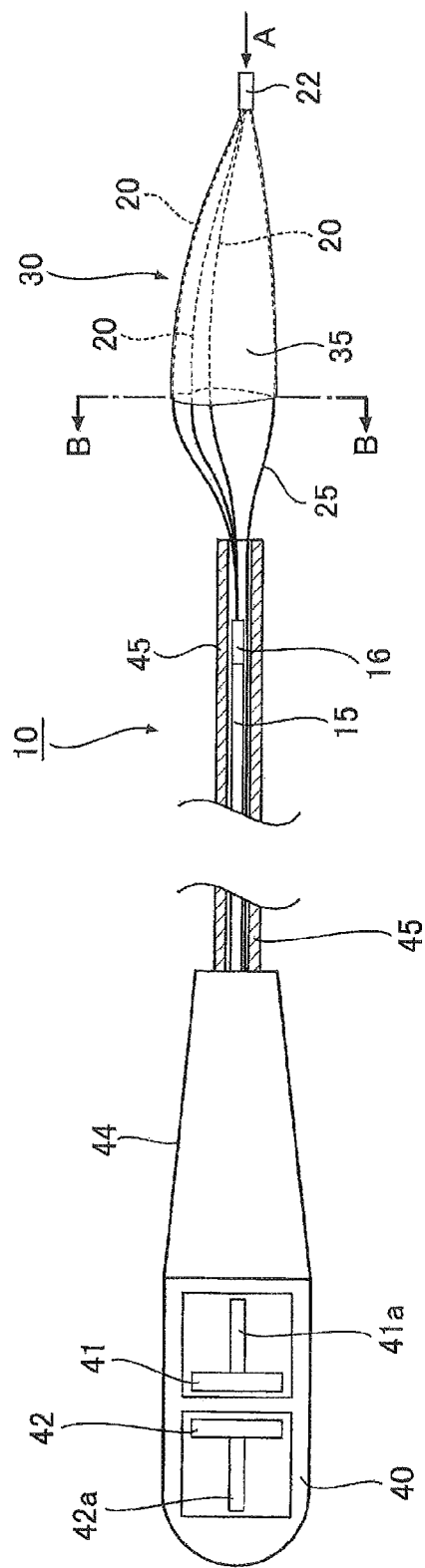
FIG. 2 is a side view diagram of the foreign object capturing device.

As shown in FIGS. 1 and 2, a body-cavity foreign object capturing device (hereinafter, referred to as "foreign object capturing device 10") of the embodiment has a first operation wire 15, plural framework wire members 20, and a second operation wire 25.

The base end portions of the plural framework wire members 20 are placed on the outer circumference of a distal end portion of the first operation wire 15, and coupled to the outer circumference of the distal end portion of the first operation wire 15 by squeezing a cylindrical coupling member 16 which is placed on the outer circumference thereof.

The distal end portion of the second operation wire 25 is bundled with distal end portions of the plural framework wire members 20, and coupled to the distal end portions of the plural framework wire members 20 by squeezing a cylindrical bundling member 22 placed on the outer circumference thereof. The second operation wire 25 extends toward the base end of the first operation wire 15 while being separated from the first operation wire 15, and is operable independently from the first operation wire 15.

Figure 10:
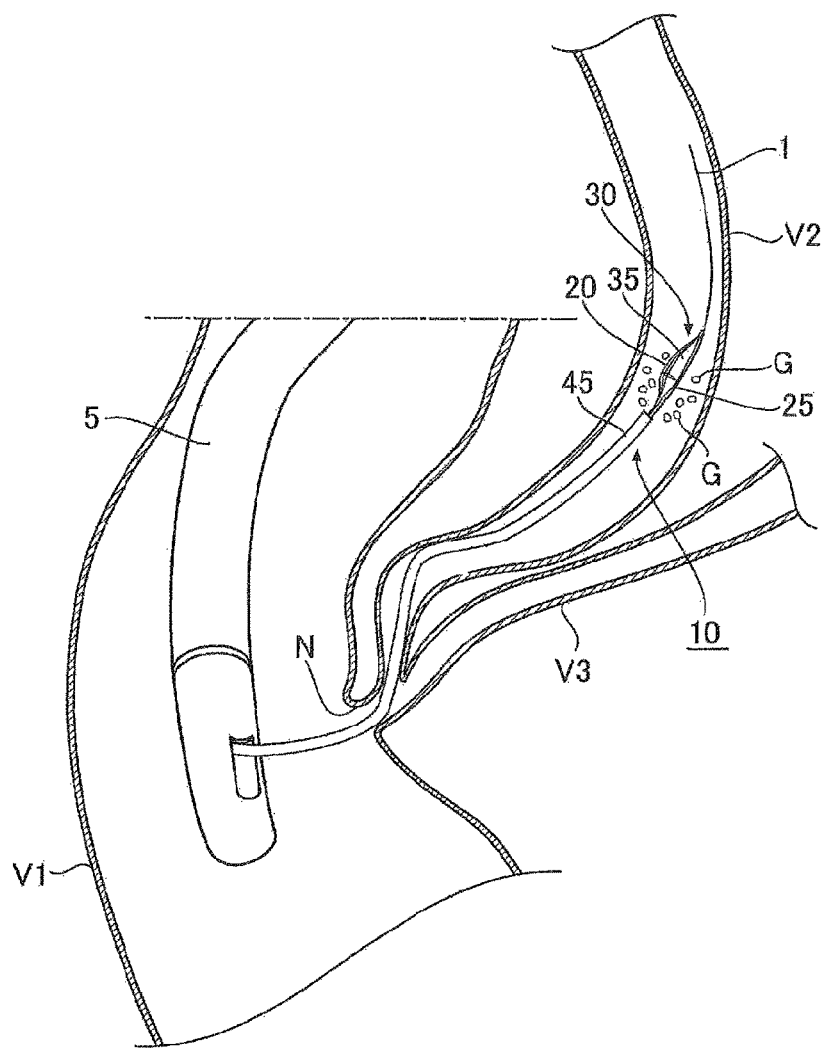
FIG. 10 is a diagram showing a first use state of the foreign object capturing device.

In the embodiment, a basket 30 is configured such that the plural framework wire members 20 is expandable by moving the first operation wire 15 relative to the second operation wire 25 toward the distal end (see FIGS. 1 and 2) for capturing foreign objects G (see FIG. 10).

The term "moving the first operation wire 15 relative to the second operation wire 25 toward the distal end" includes operations such as (1) the second operation wire 25 is fixed, and the first operation wire 15 is pushed toward the distal end, (2) the first operation wire 15 is fixed, and the second operation wire 25 is pulled toward the base end, and (3) the first operation wire 15 is pushed toward the distal end, and the second operation wire 25 is pulled toward the base end.

The coupling between the base end portions of the framework wire members 20 and the distal end portion of the first operation wire 15, and that between the distal end portions of the framework wire members 20 and the distal end portion of the second operation wire 25 may be performed by, for example, an adhesive agent, brazing, soldering, or a string-like member, and are not particularly limited.

Figure 3:
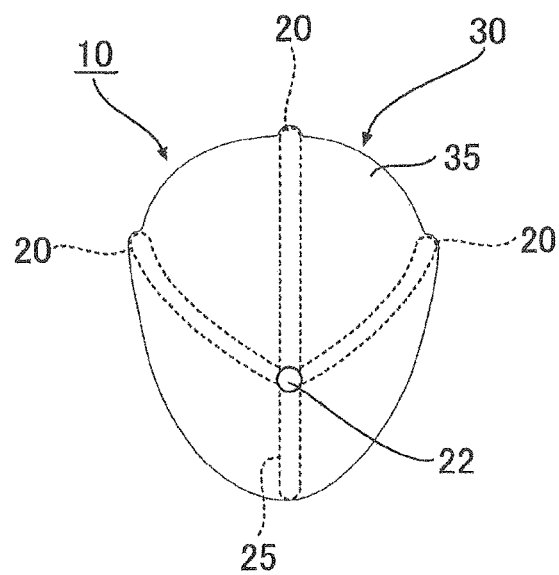
FIG. 3 is a main-portion enlarged diagram of the foreign object capturing device, as viewed along arrow line A in FIG. 2.
Figure 4:
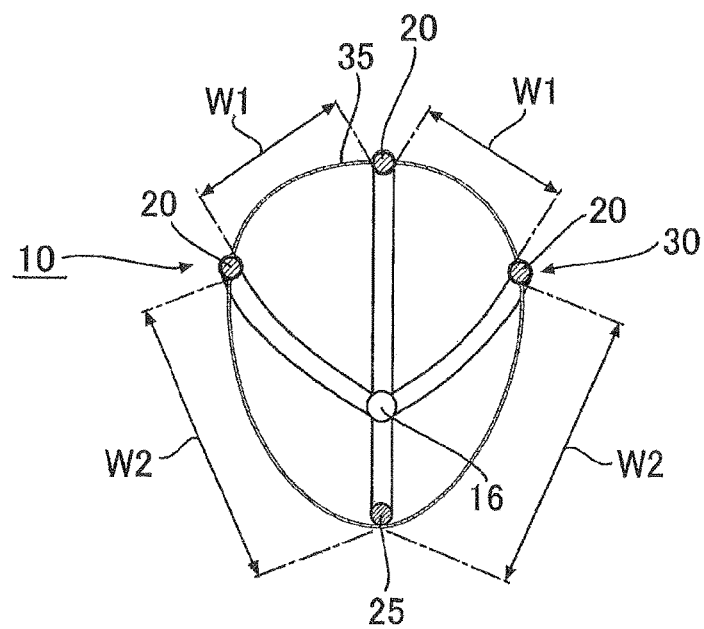
FIG. 4 is a main-portion enlarged diagram of the foreign object capturing device, as viewed along arrow line B-B in FIG. 2.

Referring also to FIGS. 3 and 4, the framework wire members 20 in the embodiment are placed, in a state where the diameter of the basket 30 is expanded, in a plural number at predetermined intervals along the circumferential direction thereof. In the embodiment, three framework wire members 20 are placed at uniform intervals W1 (see FIG. 4) in the circumferential direction. However, the placement manner is not limited to this. The interval W1 in the state where the diameter of the basket 30 is expanded is varied depending on a place in the body where the foreign object capturing device 10 is to be used. Usually, the interval is preferably 3 to 20 mm, more preferably 3 to 15 mm.

Each of the framework wire members 20 is formed by a wire member which is thinner than the second operation wire 25 (see FIGS. 3 and 4). Specifically, the outer diameter of the framework wire member 20 is preferably 0.02 to 0.1 mm, more preferably 0.05 to 0.1 mm.

The number of the framework wire members 20 is preferably 2 to 4, more preferably 2 or 3.

On the other hand, the second operation wire 25 in the embodiment is configured by a single wire member, and placed in a position circumferentially opposed to a portion where the plural framework wire members 20 are placed in the state where the diameter of the basket 30 is expanded (see FIGS. 3 and 4).

The interval W2 (see FIG. 4) between the second operation wire 25 and the framework wire member 20 which is closest to the second operation wire 25 is wider than the intervals W1 between adjacent framework wire members 20, 20. The interval W2 in the state where the diameter of the basket 30 is expanded is varied depending on a place in the body where the foreign object capturing device 10 is to be used. Usually, the interval is preferably 5 to 30 mm, more preferably 10 to 25 mm.

The number of the second operation wire 25 is not limited to one. Plural wires may be bundled together and placed, and the placement interval is not limited to the above-described manner. In the case where the second operation wire 25 is configured by a single wire member, the outer diameter is preferably 0.05 to 0.2 mm, more preferably 0.05 to 0.15 mm.

The basket 30 shown in FIG. 2 is configured so that the depth of the basket 30 is reduced by further moving the first operation wire 15 relative to the second operation wire 25 toward the distal end (see FIGS. 6 to 9). The depth of the basket 30 means the axial length from the coupling portion between the distal end portions of the plural framework wire members 20 and the distal end portion of the second operation wire 25, to a portion where the diameter of the basket 30 is maximally expanded.

The first operation wire 15, the second operation wire 25, and the framework wire members 20 are formed by, for example, stainless steel, Ta, Ti, Pt, Au, W, or a shape memory alloy such as a Ni—Ti based alloy, a Co—Cr based alloy, a Co—Cr—Ni based alloy, a Cu—Zn—X (X=Al, Fe, etc.) based alloy, or a Ni—Ti—X (X=Fe, Cu, V, Co, etc.) based alloy. The coupling member 16 and the bundling member 22 are formed by a radiopaque metal, for example, Pt, Ti, Pd, Rh, Au, W, or an alloy thereof.

The basket 30 is preferably configured such that the plural framework wire members 20 are previously shaped so as to form an approximate spindle shape as shown in FIG. 2 in cooperation with the second operation wire 25, whereby the distal and base end sides are contracted, and the diameter of a portion that is close to the axial base end is expanded. More preferably, the above-described shape memory alloy is used as the framework wire members 20, and a shape memory process is performed so as to cause it to memorize the above-described shape.

A resin membrane 35 is disposed in a portion of the basket 30 which ranges from the coupling portion between the distal end portions of the plural framework wire members 20 and the distal end portion of the second operation wire 25, to the portion where the diameter of the basket 30 is maximally expanded. In the embodiment, the resin membrane 35 is disposed so as to cover the portion between the plural framework wire members 20 and the second operation wire 25, and has a bag-like shape in which the distal end side is closed, the diameter is gradually expanded as advancing toward the base end side, and the base end side is opened, and the diameter is expanded in accordance with the expansion of the diameter of the basket 30. Even in the case where the foreign object G received through the opening of the basket 30 is relatively small, the resin membrane 35 enables the foreign object to be captured so as not to be discharged gaps from between the plural framework wire members 20 and the second operation wire 25.

The resin membrane 35 in the embodiment is configured so as to cover the outer circumferences of the framework wire members 20 and the second operation wire 25 (a state where the framework wire members 20 and the second operation wire 25 are so to speak embedded in the resin membrane 35). However, the mode of the membrane is not limited to this. Plural minute holes for allowing a fluid to pass therethrough and having a size which does not allow the foreign objects G to pass may be disposed in the resin membrane 35.

As the material of the resin membrane 35, for example, polyurethane such as polyether-based polyurethane, polyester-based polyurethane, polycarbonate-based polyurethane, or polycaprolactone-based polyurethane, polyurethane elastomer, nylon, nylon elastomer, olefin-based elastomer including polybutadiene and the like, styrene-based elastomer, silicone, polyimide-based resin, polyether ketone, or polyether ether ketone may be employed. Among them, polyurethane is preferably employed.

The resin membrane 35 can be formed by, for example, casting a polymer solution in a state where the plural framework wire members 20 are previously set in molds, or setting the plural framework wire members 20 in molds, and then dipping the molds in a polymer solution.

In the foreign object capturing device 10 of the embodiment, as shown in FIG. 2, a catheter 45 is placed on the outer circumferences of the first operation wire 15 and the second operation wire 25 other than the distal end portions. Moreover, an operation handle 40 for operating the first operation wire 15 and the second operation wire 25 independently from each other is placed on the base end side of the catheter 45.

The catheter 45 in the embodiment is a so-called single-lumen catheter in which one lumen is disposed in a range from the base end to the distal end as shown in FIG. 2. Alternatively, plural lumens may be disposed. The lumen structure is not particularly limited. In the case where two lumens are disposed, for example, the first operation wire 15 is passed through a predetermined one of the lumens, and the second operation wire 25 is passed through the other lumen, thereby causing the first operation wire 15 and the second operation wire 25 not to tangle with each other, and the operability can be improved.

In the operation handle 40, as shown in FIGS. 1 and 2, a first slider 41 is attached to a distal end side thereof through a slit 41a so as to be anteroposteriorly slidable in the axial direction of the operation handle 40, and a second slider 42 is attached to a position adjacent to the first slider 41 through a slit 42a so as to be anteroposteriorly slidable in the axial direction of the operation handle 40. The base end portion of the first operation wire 15 is connected to the first slider 41 through a through hole which is formed in the operation handle 40, and which is not shown, and on the other hand the base end portion of the second operation wire 25 is connected to the second slider 42 through a through hole which is not shown.

Figure 5:
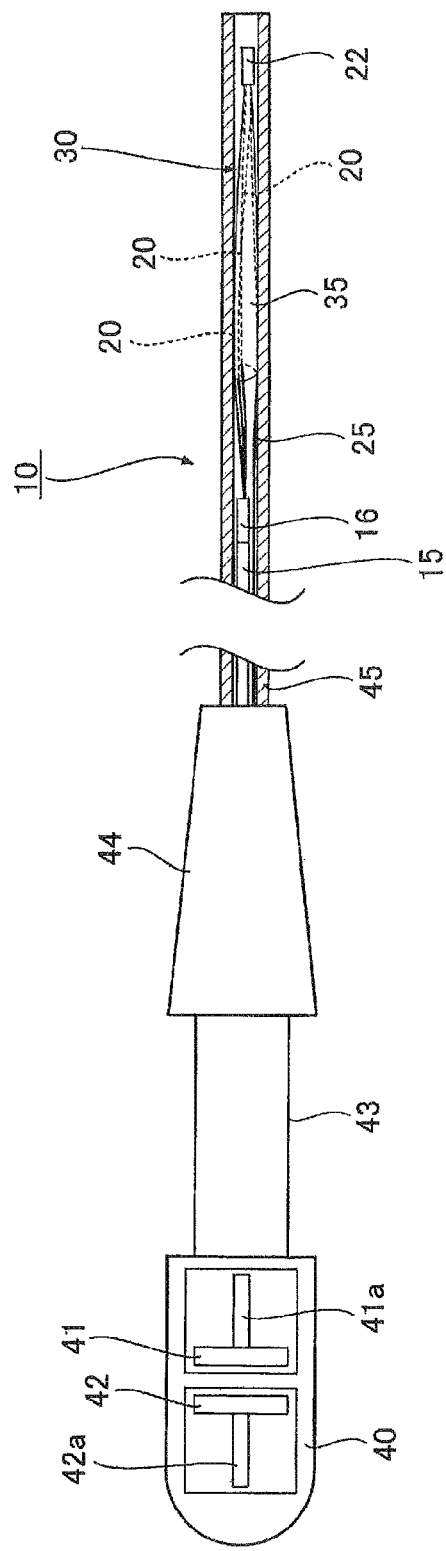
FIG. 5 is a side view diagram of a state where a basket is accommodated in a distal end portion of a catheter, and showing an operation of the foreign object capturing device.

As shown in FIG. 5, a tubular portion 43 which has a slightly small outer diameter extends from the distal end side of the operation handle 40, and a slide member 44 which is slidable with respect to the tubular portion 43, and which has a tapered cylindrical shape is attached to the outer circumference of the tubular portion 43. A base end portion of the catheter 45 is coupled to the slide member 44. When the slide member 44 is slid toward the distal end of the tubular portion 43, therefore, the catheter 45 is pushed out, and the framework wire members 20 are linearly stretched to reduce the diameter so that the basket 30 is accommodated in the inner circumference of a distal end portion of the catheter 45 (see FIG. 5).

Although not illustrated, it is preferable that, for example, an engagement button is disposed in the slide member 44, on the other hand an engagement recess which is engageable with the engagement button is disposed in the distal end of the tubular portion 43, and, when the slide member 44 is slid toward the base end of the tubular portion 43, the engagement button is engaged with the engagement recess to restrict the sliding operation of the slide member 44.

In a state where the diameter of the basket 30 is expanded as shown in FIG. 2, the first slider 41 is placed in a position closer to the base end of the handle, and the second slider 42 is placed in a position closer to the distal end of the handle.

Figure 6:
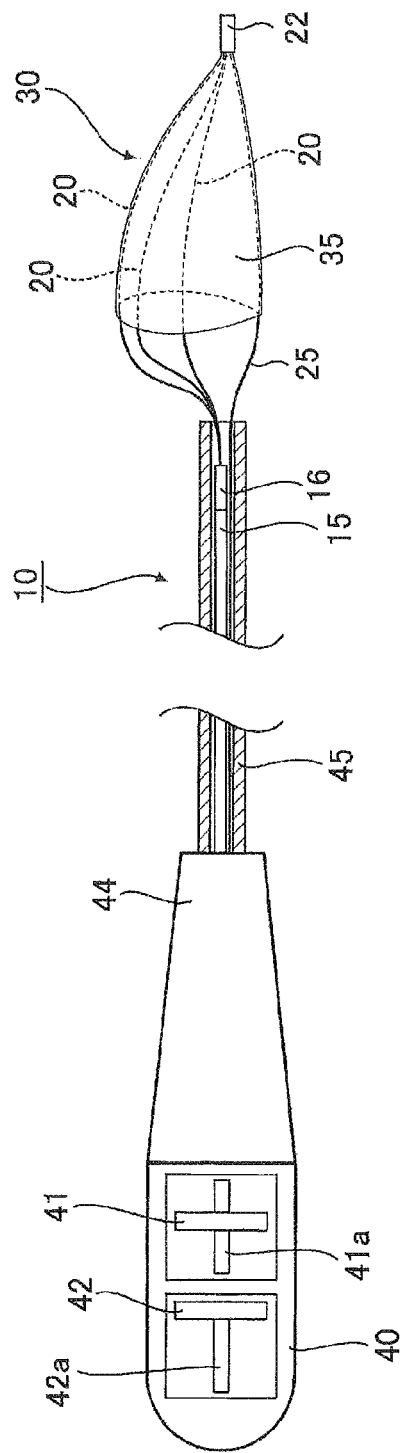
FIG. 6 is a side view diagram of a state where the diameter of the basket is expanded in the state of FIG. 2, and showing an operation of the foreign object capturing device.
Figure 7:
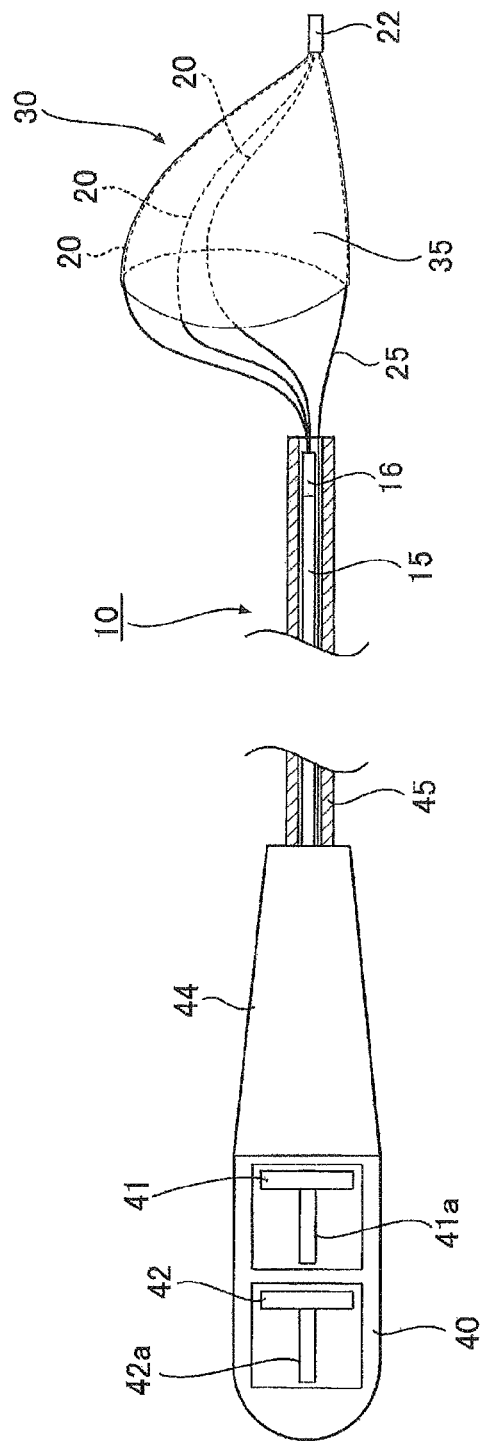
FIG. 7 is a side view diagram of a state where the diameter of the basket is expanded in the state of FIG. 6, and showing an operation of the foreign object capturing device.

When, in the diameter-expanded state of the basket 30 shown in FIG. 2, the second slider 42 is held, and the first slider 41 is slid toward the distal end, the first operation wire 15 is moved toward the distal end with respect to the second operation wire 25, and the diameter of the basket 30 is expanded (see FIG. 6). When, in this state, the first slider 41 is further slid toward the distal end, the first operation wire 15 is further moved toward the distal end with respect to the second operation wire 25, and the diameter of the basket 30 is further expanded (see FIG. 7).

Figure 8:
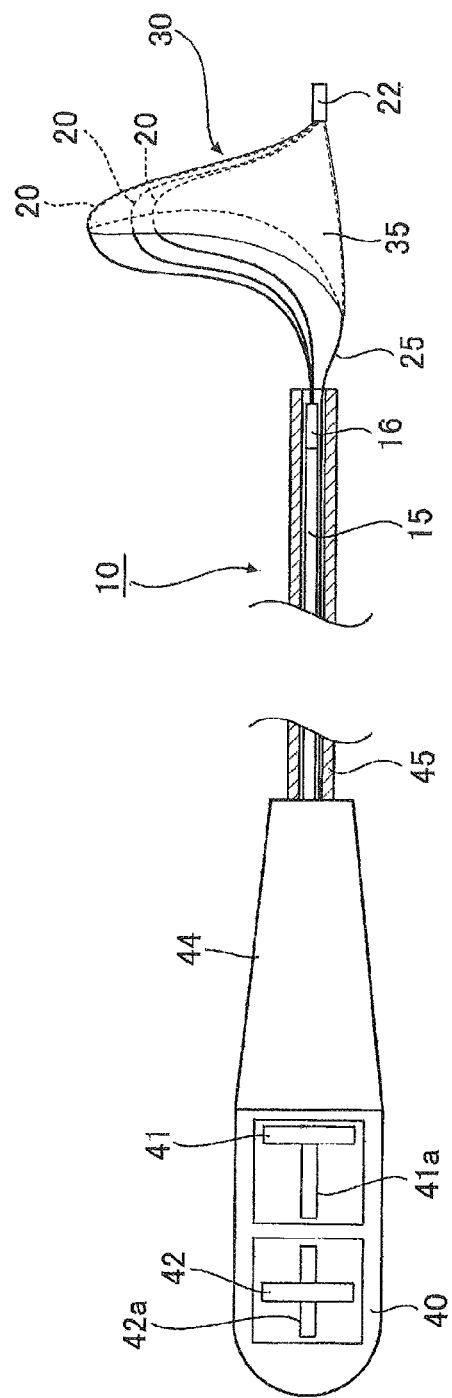
FIG. 8 is a side view diagram of a state where the diameter of the basket is further expanded in the state of FIG. 7, and showing an operation of the foreign object capturing device.

When, in the above-described state, the first slider 41 is held, and the second slider 42 is slid toward the base end, the second operation wire 25 is moved toward the base end with respect to the first operation wire 15, and the diameter is largely expanded so that the basket 30 is pressed to have a flat shape (see FIG. 8). When, in this state, the second slider 42 is further slid toward the base end, the second operation wire 25 is further moved toward the base end with respect to the first operation wire 15, and the diameter is further largely expanded so that a part of the basket 30 rolls back toward the distal end (see FIG. 9).

The structure and shape of the operation handle 40 are not limited to the above-described mode as far as the first operation wire 15 and the second operation wire 25 are operable independently from each other.

When, in the diameter-expanded state of the basket 30 shown in FIG. 2, the slide member 44 is slid toward the distal end with respect to the tubular portion 43 of the operation handle 40, the catheter 45 is pushed out, the outer circumference of the basket 30 is pressed, the framework wire members 20 are linearly stretched to reduce the diameter, and the basket 30 is accommodated in the inner circumference of the distal end portion of the catheter 45. On the other hand, when the slide member 44 is slid toward the base end with respect to the tubular portion 43, the basket 30 is released from the distal end portion of the catheter 45 to expand the diameter (see FIG. 2). A lumen through which a guide wire 1 (see FIG. 10) can be passed, and which is not shown is disposed in the catheter 45.

In the embodiment, the catheter 45 is coupled to the slide member 44 of the operation handle 40, and the catheter 45 is slid by the sliding operation of the slide member 44. Alternatively, for example, the operation handle 40 and the catheter 45 may be separately formed, and the catheter 45 may be made independently slidable. Alternatively, a tube, sheath, or the like which is separately formed may be placed on the outer circumference of the catheter 45, and the basket 30 may be accommodated or released by the sliding operation thereof.

Next, an example of the method of using the thus configured foreign object capturing device 10 of the invention will be described.

As shown in FIG. 10, the foreign object capturing device 10 of the embodiment can be used for capturing foreign objects G such as gallstones produced in a cavity of the human body, for example, a tubular organ V2 such as the bile duct, the pancreatic duct, a ureter, a trachea, or a blood vessel such as a brain blood vessel, the thoracic aorta, or the abdominal aorta, and moving the foreign objects G to a tubular organ V1 having a relatively-large inner diameter such as the duodenum to discharge the foreign objects. The place to which the foreign object capturing device 10 is to be applied is not particularly limited. However, it may be particularly preferably used for discharge a gallstone in the bile duct or a pancreatic stone in the pancreatic duct.

When the foreign object capturing device 10 is to be used, as shown in FIG. 5, the slide member 44 is firstly slid toward the distal end of the tubular portion 43, the catheter 45 is pushed out to cause the framework wire members 20 to be linearly stretched, and the basket 30 in the diameter-contracted state is accommodated in the inner circumference of the distal end portion of the catheter 45.

Then, an endoscope 5 is moved by a well-known method from the oral cavity to the tubular organ V1 having a large diameter such as the duodenum through the stomach and the like, and a distal end portion of the endoscope 5 is placed in the vicinity of a branch portion N (the papilla) of tubular organs V2, V3.

Thereafter, the guide wire 1 is ejected from the distal end opening of the endoscope 5 through the lumen, and inserted into the tubular organ V2 (bile duct), and the distal end portion is caused to reach a position which is across the portion where the plural foreign objects G exist. Thereafter, the guide wire 1 is inserted into the not-shown lumen of the catheter 45, the foreign object capturing device 10 is moved along the guide wire 1 under observation through the endoscope 5, and the distal end portion of the catheter 45 is caused to reach a position which is across the portion where the plural foreign objects G exist.

When, in the above-described state, the slide member 44 is slid toward the base end with respect to the tubular portion 43 of the operation handle 40, the basket 30 is released from the distal end portion of the catheter 45, and the plural framework wire members 20 and the resin membrane 35 are widened to expand the diameter of the basket 30 (see FIGS. 2 and 10).

When the first slider 41 of the operation handle 40 is slid toward the distal end while holding the second slider 42, the first operation wire 15 is moved toward the distal end with respect to the second operation wire 25, and the diameter of the basket 30 is expanded (see FIG. 6). When, in this state, the first slider 41 is further slid toward the distal end, the first operation wire 15 is further moved toward the distal end with respect to the second operation wire 25, and the diameter of the basket 30 is further expanded (see FIGS. 7 and 11).

Figure 11:
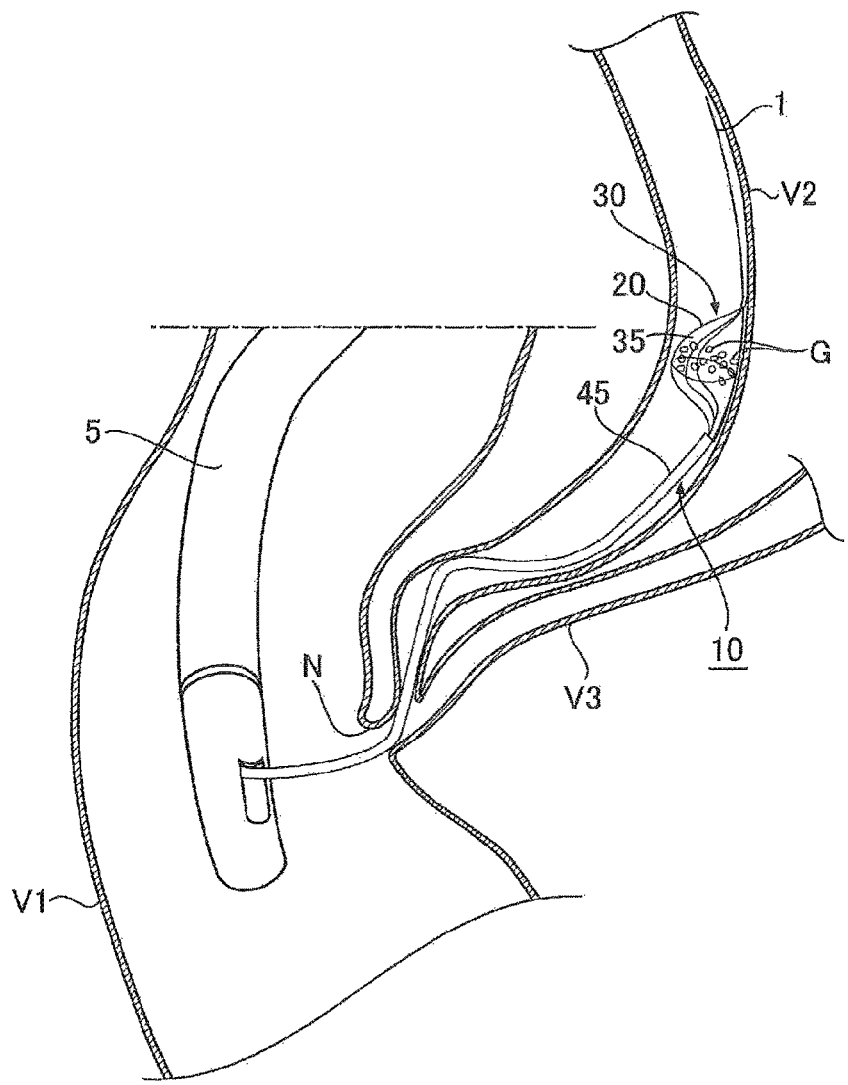
FIG. 11 is a diagram showing a second use state of the foreign object capturing device.

When, in the above-described state, the whole foreign object capturing device 10 is pulled toward the proximal side, the foreign objects G enter through the openings of the basket 30 as shown in FIG. 11, and it is possible to capture the foreign objects G.

In the foreign object capturing device 10, as described above, the basket 30 is configured such that the plural framework wire members 20 is expanded by moving the first operation wire 15 relative to the second operation wire 25 toward the distal end. When, in this state, the whole foreign object capturing device 10 is pulled toward the proximal side, therefore, the foreign objects G enter through the openings of the basket 30 as shown in FIG. 11, and it is possible to capture the foreign objects G.

In the embodiment, the plural framework wire members 20 are formed by wire members which are thinner than the second operation wire 25 (see FIGS. 3 and 4), and therefore the diameter of the basket 30 can be easily expanded.

In the embodiment, moreover, the single second operation wire 25 is placed so as to be circumferentially opposed to the plural framework wire members 20, and the interval W2 between the second operation wire 25 and the framework wire member 20 which is closest to the second operation wire 25 is wider than the intervals W1 between the framework wire members 20, 20 (see FIG. 4). Therefore, the diameter of the basket 30 is expanded so that the basket expands in the circumferential direction, the large openings can be ensured, and even a large foreign object can be easily captured.

Figure 12:
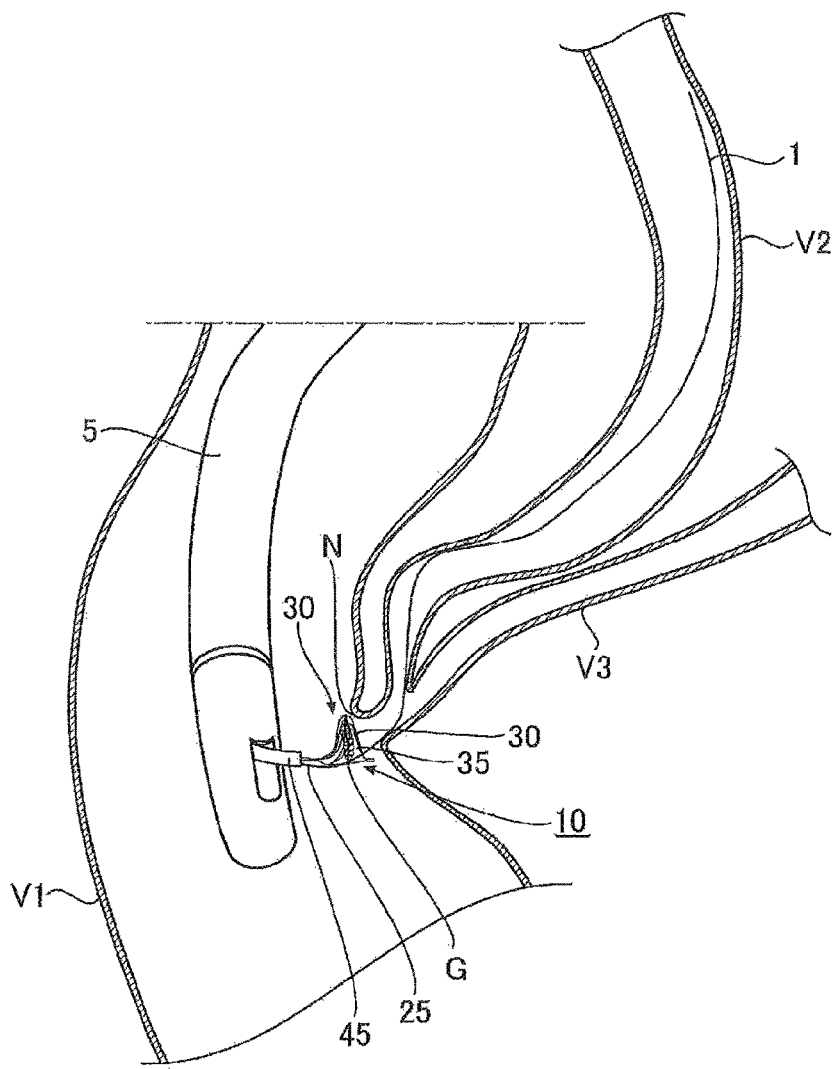
FIG. 12 is a diagram showing a third use state of the foreign object capturing device.

After the foreign objects G are captured by the basket 30 as described above, the whole foreign object capturing device 10 is further pulled back toward the proximal side, and the plural framework wire members 20 and the resin membrane 35 are moved to the tubular organ V1 (for example, the duodenum) having a diameter which is larger than the tubular organ V2 (see FIG. 12).

When, in this position, the second slider 42 of the operation handle 40 is slid toward the base end while holding the first slider 41, the second operation wire 25 is moved toward the base end with respect to the first operation wire 15, and the diameter is largely expanded so that the basket 30 is pressed to have a flat shape as shown in FIGS. 8 and 12.

Figure 9:
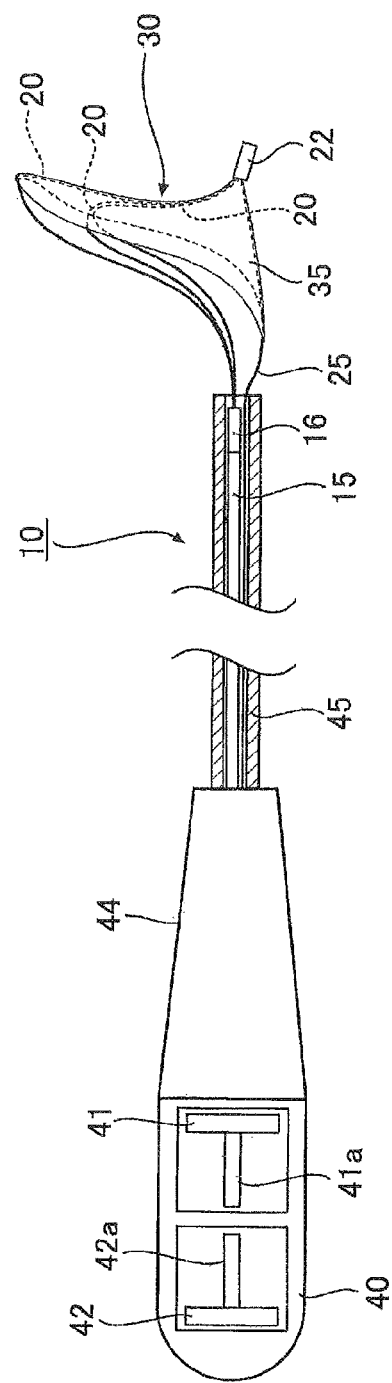
FIG. 9 is a side view diagram of a state where the diameter of the basket is further expanded in the state of FIG. 8, and showing an operation of the foreign object capturing device.
Figure 13:
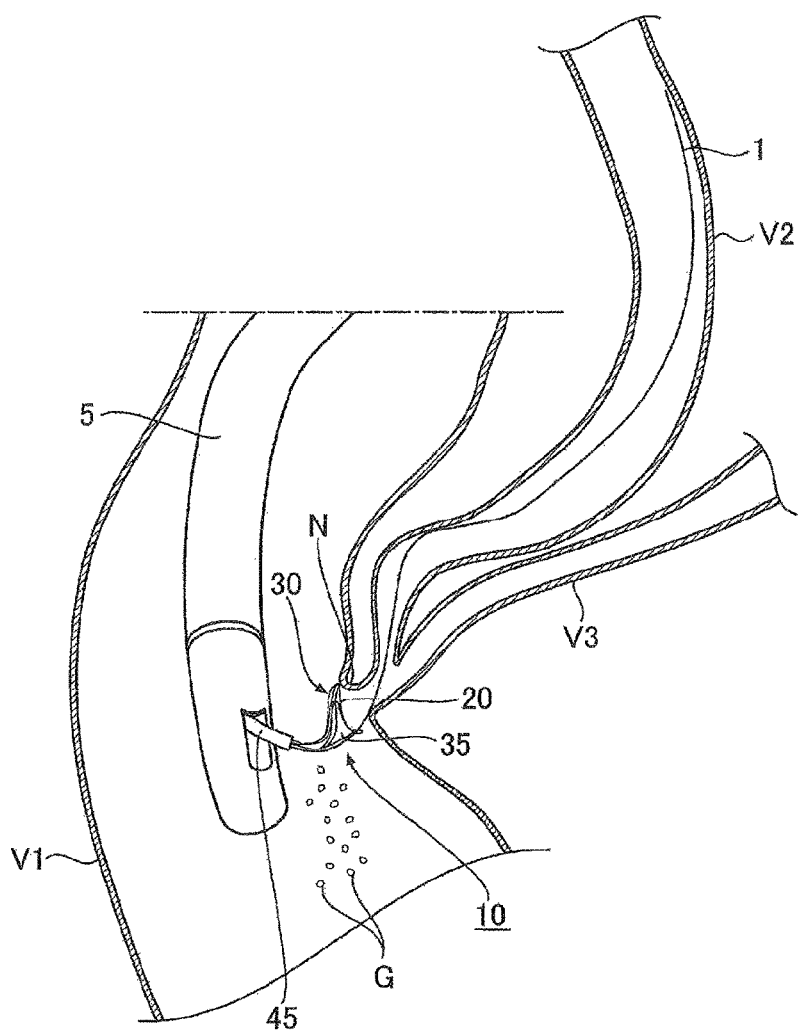
FIG. 13 is a diagram showing a fourth use state of the foreign object capturing device.

When, in this state, the second slider 42 of the operation handle 40 is further slid toward the base end while holding the first slider 41, the second operation wire 25 is further moved toward the base end with respect to the first operation wire 15, and the diameter is further largely expanded so that a part of the basket 30 rolls back toward the distal end as shown in FIGS. 9 and 13.

As a result, the foreign objects G captured in the basket 30 can be smoothly pushed out through the openings, and discharged into the tubular organ V1 as shown in FIG. 13. In the case where the foreign objects G cannot be sufficiently discharged by the above-described operation, the diameter of the basket 30 can be expanded and contracted, and the foreign objects G can be discharged from the interior of the resin membrane 35 by, in a state where the first slider 41 of the operation handle 40 is fixed, repeatedly anteroposteriorly sliding the second slider 42 in the axial direction.

In the embodiment, the resin membrane 35 is disposed in the basket 30. Even when the foreign objects G are relatively small substances such as fragmentary stones, debris, or plaque, therefore, the foreign objects can be captured without omission.

When a large foreign object G or a large number of foreign objects G are captured in the basket 30, there is a possibility that the basket 30 may be caught in a small-inner diameter place (for example, the papilla) in a tubular organ, and may not be taken out. In this case, the resin membrane 35 is broken, and the foreign objects G are discharged. Therefore, the basket 30 can be safely taken out.

FIGS. 14 to 22 show another embodiment of the body-cavity foreign object capturing device according to invention. Portions which are substantially identical with the above-described embodiment are denoted by the same reference numerals, and their description is omitted.

Figure 14:
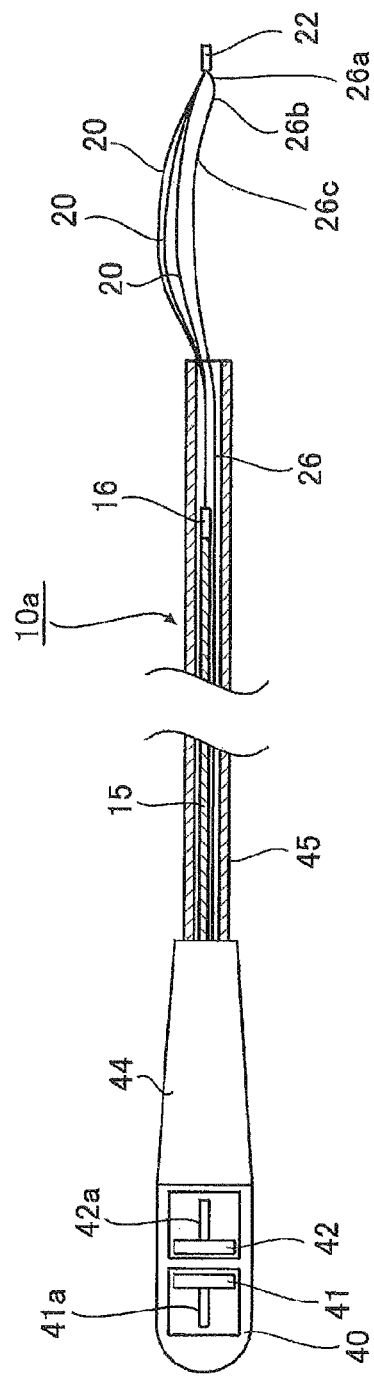
FIG. 14 is a side view diagram showing another embodiment of the body-cavity foreign object capturing device according to the invention.

As shown in FIG. 14, the body-cavity foreign object capturing device 10a (hereinafter, referred to as "foreign object capturing device 10a") of the embodiment has: the first operation wire 15; the plural framework wire members 20 in which the base end portions are coupled to the distal end portion of the first operation wire 15 through the coupling member 16, and the distal end portions are bundled together through the bundling member 22; and a second operation wire 26 which is coupled to the distal end portions of the plural framework wire members 20 through the bundling member 22, which extends toward the base end of the first operation wire 15 while being separated from the first operation wire 15, and which is operable independently from the first operation wire 15.

The foreign object capturing device 10a of the embodiment has a structure in which the resin membrane 35 is not stretched among the plural framework wire members 20. In the operation handle 40 in the embodiment, the second slider 42 for operating the second operation wire 26 is placed in a distal end side thereof, and the first slider 41 for operating the first operation wire 15 is placed in a position adjacent to the second slider 42 (the positional relationship is opposite to that of the above-described embodiment).

Figure 15:
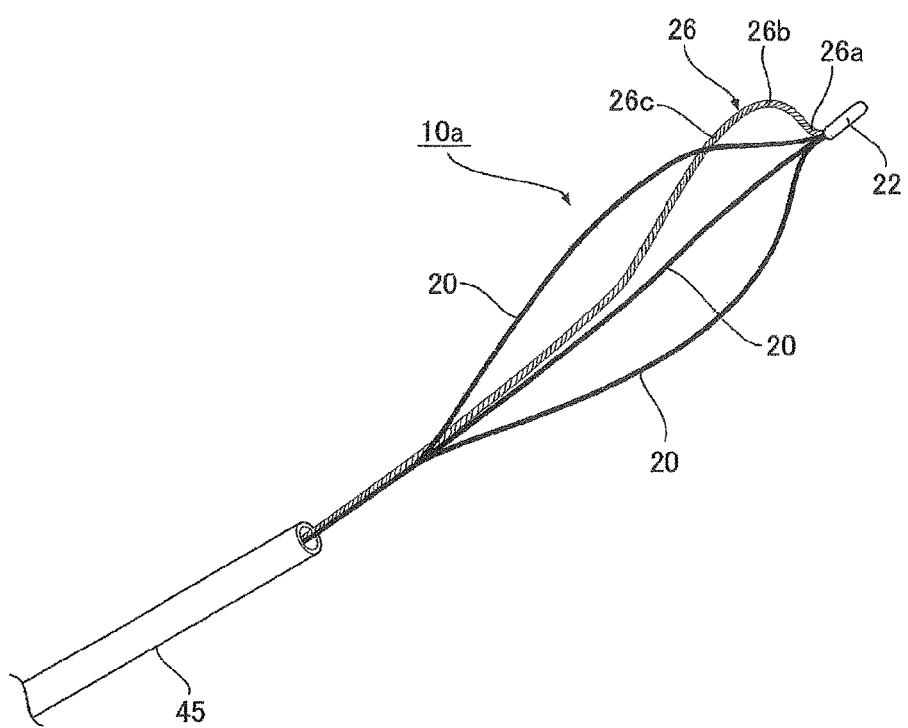
FIG. 15 is a main-portion enlarged perspective view of the foreign object capturing device in a state where a second operation wire is in a free state.
Figure 16:
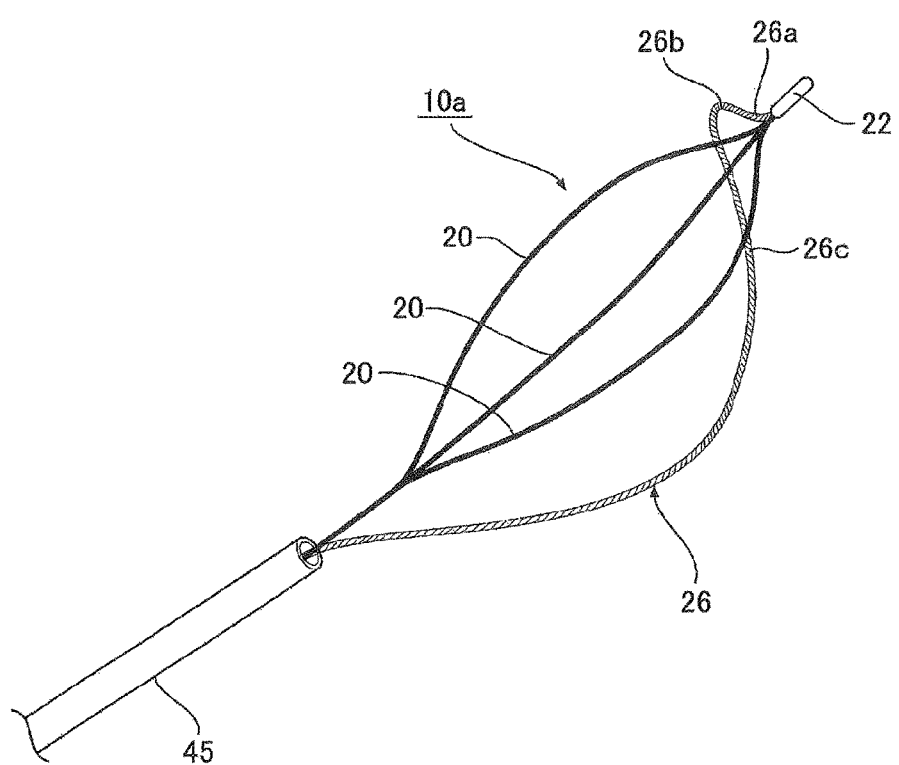
FIG. 16 is a main-portion enlarged perspective view of the foreign object capturing device in a state where the second operation wire is moved toward the distal end.

The foreign object capturing device 10a has a shape in which the distal end side of the second operation wire 26 is caused to have a predetermined curved shape as an initial shape (see FIG. 15). Namely, as shown in FIG. 17A, the second operation wire 26 is caused to have a curved shape as an initial shape, which expands in the outer circumference and circumferentially extends, as viewed from the axial distal end side, in a free state where the second operation wire 26 is not operated (a state where the second slider 42 is placed in a position closer to the base end of the handle).

Figure 17A:
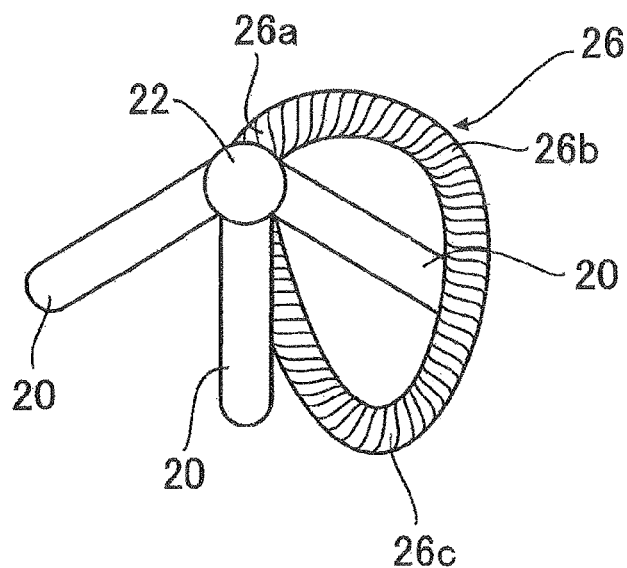
FIGS. 17A and 17B show the foreign object capturing device as viewed from the axial distal end side.
Figure 17B:
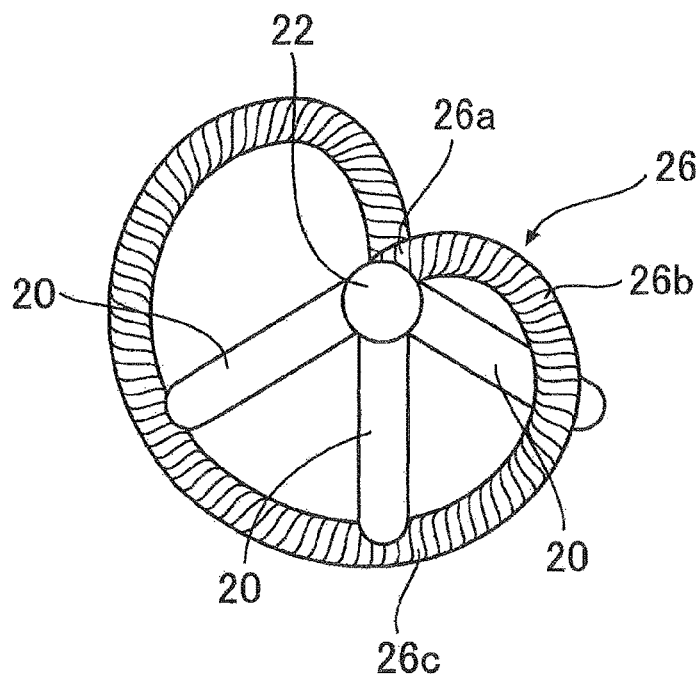

As shown in FIGS. 15 and 17A, the curved shape of the second operation wire 26 in the embodiment has: a distal end portion 26a which is bent in the outer radial direction from the bundling member 22 that is a coupling portion between the plural framework wire members 20 and the second operation wire 26; a bent portion 26b which extends in the circumferential direction from the distal end portion 26a while expanding; and a curved portion 26c which extends from the bent portion 26b and returns toward the base end of the first operation wire 15 while being gently curved (see FIG. 15) so as to pass outside a predetermined one of the framework wire members 20. The shape of the second operation wire 26 is not limited to this mode. For example, the curved portion 26c may be caused to have a spiral shape with plural loops as an initial shape. However, it is preferable that the wire has at least the distal end portion 26a which is bent in the outer radial direction from the coupling portion, the bent portion 26b which extends in the circumferential direction while expanding, and the curved portion 26c which returns toward the base end of the first operation wire 15.

The foreign object capturing device 10a is configured so that the second operation wire 26 expands in the outer radial direction by moving the second operation wire 26 relative to the first operation wire 15 toward the distal end (see FIGS. 16, 17B, 18A, 18B and 19A), and the second operation wire 26 is moved to the distal end side with respect to the coupling portion (bundling member 22) between the distal ends of the plural framework wire members 20 and the distal end of the second operation wire 26 by further relatively moving the second operation wire 26 toward the distal end (see FIG. 19B).

Figure 18A:
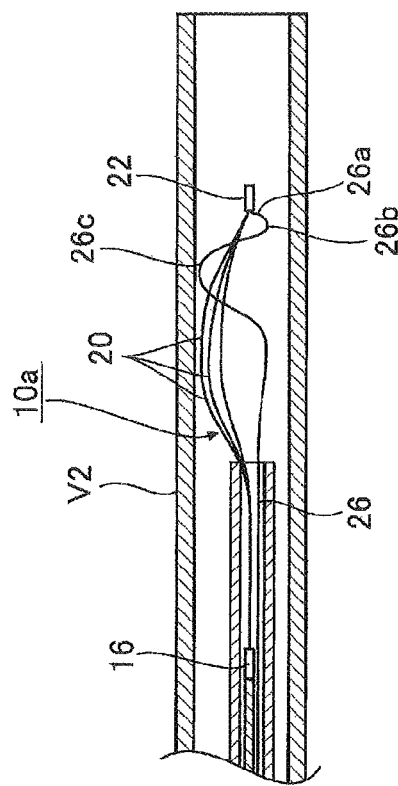
FIGS. 18A and 18B show an operation of the foreign object capturing device.
Figure 18B:
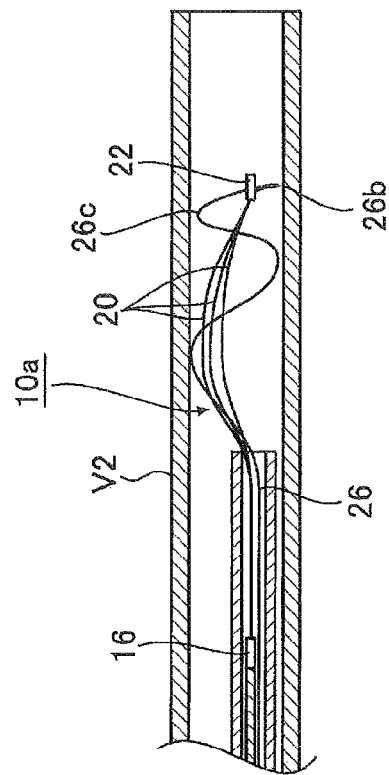

In the embodiment, the second operation wire 26 is moved in the following manner. That is, when, in a free state which is shown in FIG. 14, and in which the second operation wire 26 is not operated, the second operation wire 26 is moved toward the distal end with respect to the first operation wire 15, the second operation wire 26 expands in the outer radial direction as shown in FIG. 18A, and the curved portion 26c butts against the inner wall of the tubular organ V2 to be curved. When the second operation wire 26 is further moved toward the distal end, the curved portion 26c of the second operation wire 26 butts against the inner wall of the tubular organ V2 to be further curved as shown in FIG. 18B, and spirally expands along the inner wall of the tubular organ V2. When the second operation wire 26 is further moved toward the distal end, the curved portion 26c is moved toward the distal end so that the loop interval of the curved portion 26c is narrowed as shown in FIG. 19A. When the second operation wire 26 is further moved toward the distal end, the curved portion 26c of the second operation wire 26 is moved to the distal end side with respect to the bundling member 22 as shown in FIG. 19B.

For the sake of convenience, FIGS. 18A, 18B and 19A show a state where a stone K (see FIG. 19B) does not exist in the tubular organ V2.

The second operation wire 26 in the embodiment is formed by a twisted wire which is configured by twisting plural wire members. Alternatively, the second operation wire may be formed by a solid wire which is configured by a single wire, and is not particularly limited. Because the foreign object G such as a relatively-large stone is captured by causing the second operation wire 26 to tangle with the outer circumference of the stone, however, the wire is preferably formed by a twisted wire which is flexible and easily bendable, and which has stiffness of a certain degree in order to transmit the operation force.

The second operation wire 26 in the embodiment is formed by a single twisted wire which is configured by twisting plural wire members. Alternatively, the second operation wire may be formed by plural wires as shown in FIGS. 21A to 22B.

Figure 21A:
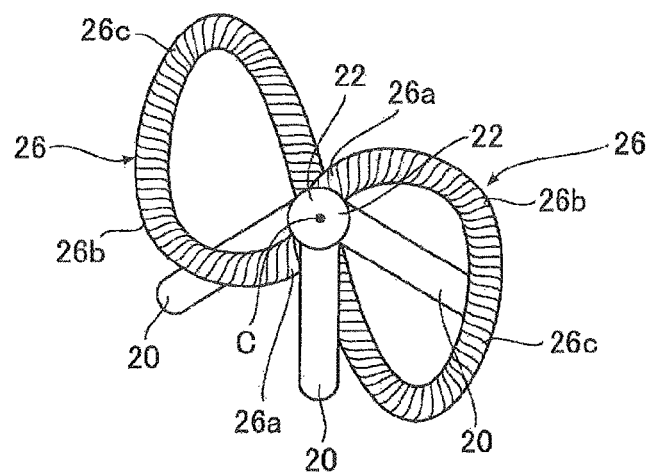
FIGS. 21A and 21B show another structure of the second operation wire in the foreign object capturing device as viewed from the axial distal end side.
Figure 21B:
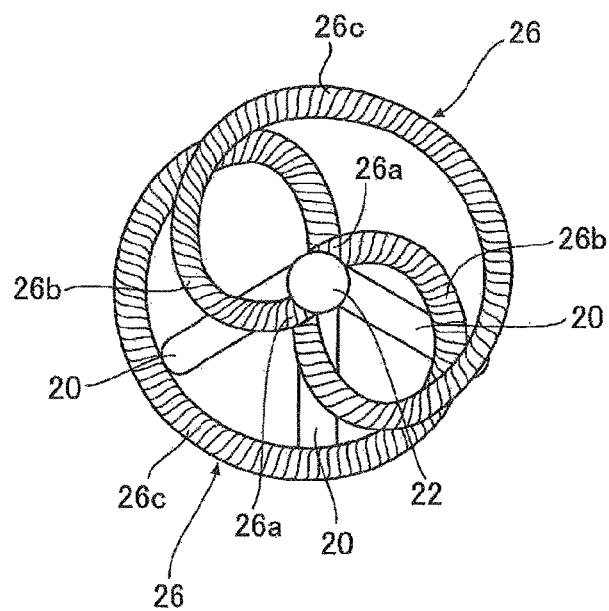

In the structure shown in FIGS. 21A and 21B, a pair of second operation wires 26, 26 are disposed which are caused to have a curved shape as an initial shape, such that they are point-symmetric about the axis C (center of the bundling member 22) of the first operation wire 15 as viewed from the axial distal end side in a free state. As shown in FIG. 21A, the pair of second operation wires 26, 26 form a substantially 8-like shape, and, in the case where the second operation wires 26 are moved toward the distal end, the curved portion 26c of each of the second operation wires 26 expands in the outer radial direction, and the whole pair of second operation wires 26 are deformed so as to exhibit a circular shape as shown in FIG. 21B.

Figure 22A:
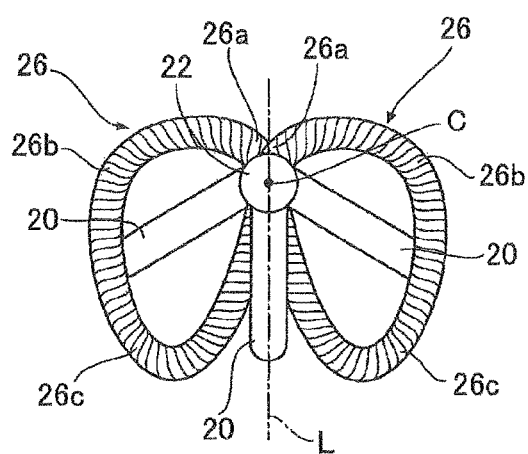
FIGS. 22A and 22B show a further structure of the second operation wire in the foreign object capturing device as viewed from the axial distal end side.
Figure 22B:
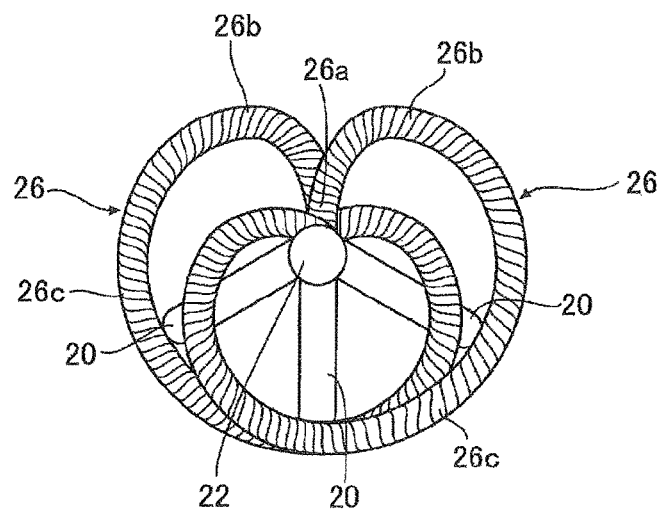

In the structure shown in FIGS. 22A and 22B, a pair of second operation wires 26, 26 are disposed, and are caused to have a curved shape as an initial shape, such that they are axisymmetric about a line L that passes through the axis C (center of the bundling member 22) of the first operation wire 15 as viewed from the axial distal end side in a free state, and that extends along the diameter expansion direction of the framework wire member 20 which is placed in the middle of the plural framework wire members 20. As shown in FIG. 22A, the pair of second operation wires 26, 26 form a shape similar to a bow knot, and, in the case where the second operation wires 26 are moved toward the distal end, the curved portion 26c of each of the second operation wires 26 expands in the outer radial direction, and the whole pair of second operation wires 26, 26 are deformed so as to exhibit a heart shape as shown in FIG. 22B.

Similarly with the second operation wire 25 in the above-described embodiment, the second operation wire 26 may be formed by, for example, stainless steel, Ta, Ti, Pt, Au, W, or a shape memory alloy such as a Ni—Ti based alloy, a Co—Cr based alloy, a Co—Cr—Ni based alloy, a Cu—Zn—X (X=Al, Fe, etc.) based alloy, or a Ni—Ti—X (X=Fe, Cu, V, Co, etc.) based alloy. Among them, a shape memory alloy is preferably used so that the second operation wire 26 is caused to have a predetermined curved shape as an initial shape. In the case where the second operation wire 26 is formed by a twisted wire, one or plural wire members in the twisted wire are preferably formed by a radiopaque metal, for example, Pt, Ti, Pd, Rh, Au, W, or an alloy thereof so that the second operation wire 26 is visible under radiation imaging.

Figure 20:
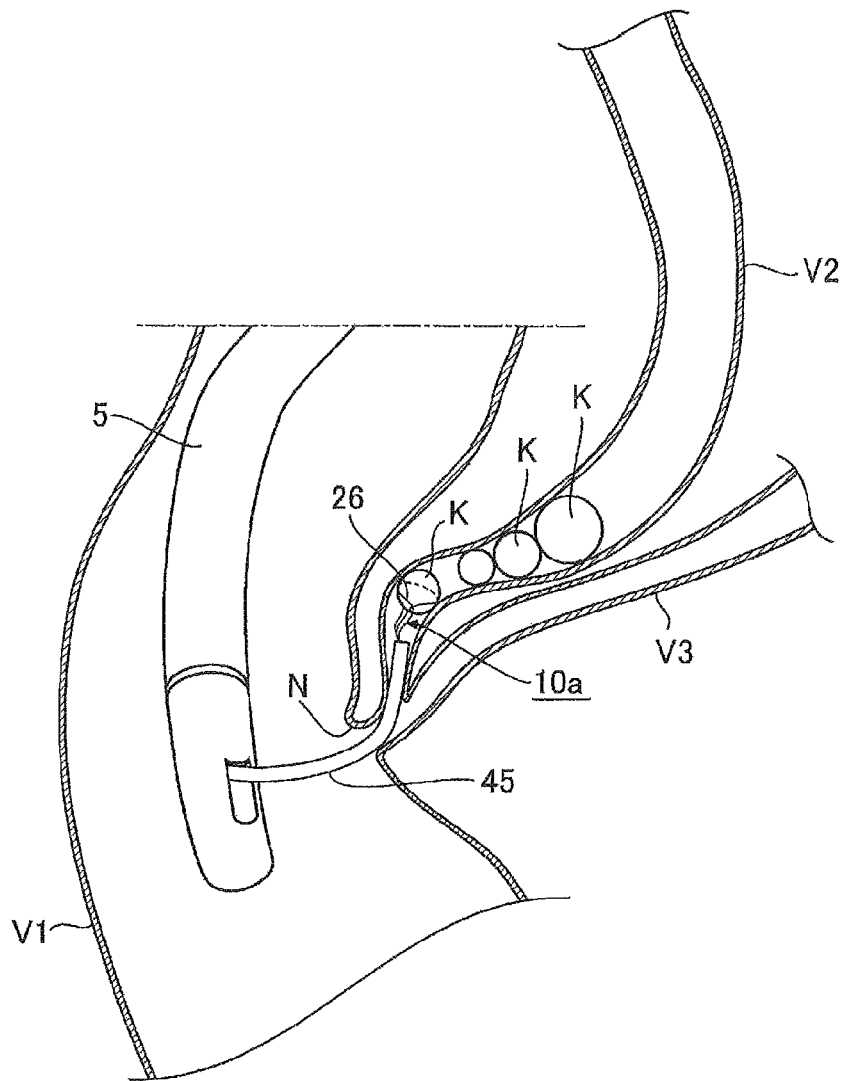
FIG. 20 is a diagram showing a use state of the foreign object capturing device.

As shown in FIG. 20, the thus structured foreign object capturing device 10a may be preferably used in the case where, with respect to so-called stacked stones in which plural stones K are produced in a line along the path of the tubular organ V2 such as the bile duct, the stones K are to be sequentially captured from the proximal side of the tubular organ V2.

This will be described with reference also to FIG. 20 and photographs (FIGS. 23 to 29) of an example (described later) of the foreign object capturing device 10a having the above-described structure. In FIGS. 23 to 29, a tube (in the following description, described as "tubular organ") modeled after a tubular organ is disposed as a body cavity, and plural stones (in the following description, described as "stones") modeled after stones are placed in the tube.

In a state where the plural framework wire members 20 and the second operation wire 26 are accommodated in the distal end portion of the catheter 45, firstly, the distal end portion of the catheter 45 is moved to the front side of the most front stone K in the stacked stones produced in the tubular organ V2, through the endoscope 5 and the guide wire 1.

Figure 23:
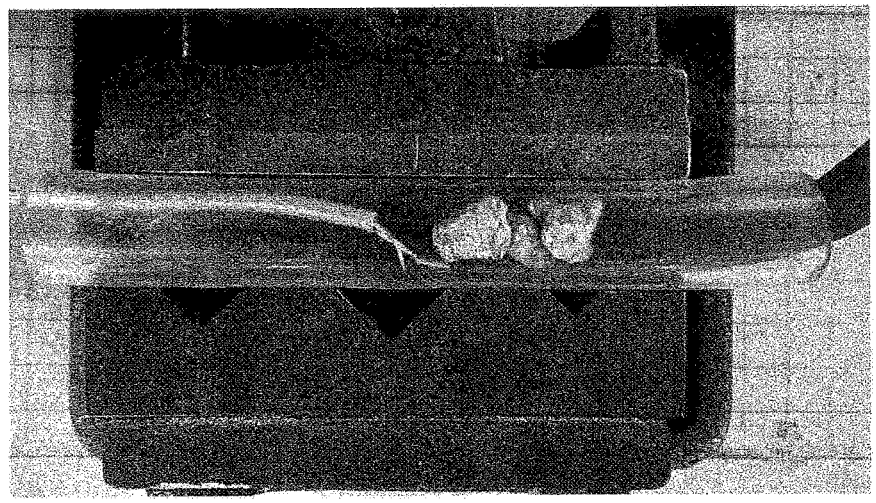
FIG. 23 is a photograph of an example of the foreign object capturing device, and showing a first use state of the example.
Figure 24:
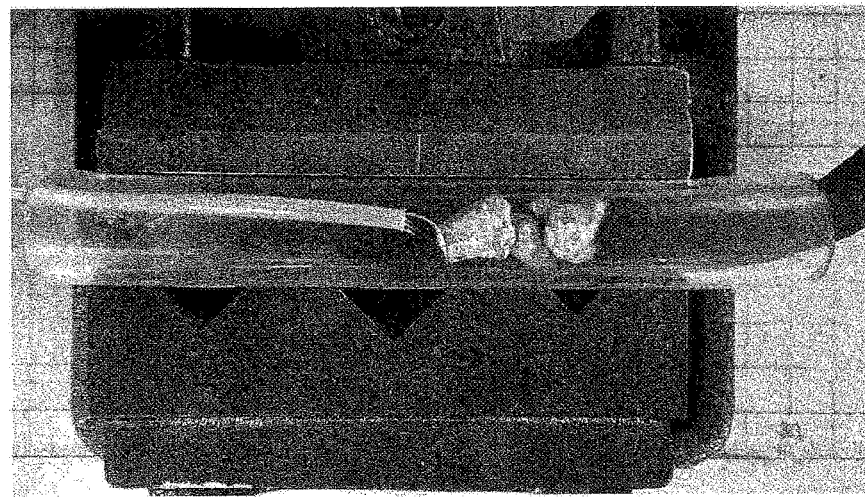
FIG. 24 is a photograph of a second use state of the foreign object capturing device.

In this state, after the plural framework wire members 20 and the second operation wire 26 are projected from the distal end opening of the catheter 45 (see FIG. 14), the bundling member 22 in the distal end is inserted between the stone K and the inner wall of the tubular organ V2 as shown in FIG. 23, and positioning of the bundling member 22 is performed.

When the second slider 42 is thereafter slid toward the distal end while holding the first slider 41, the second operation wire 26 expands in the outer radial direction, and the curved portion 26c butts against the inner wall of the tubular organ V2 to be curved (see FIG. 18A). When the second slider 42 is further slid toward the distal end, the curved portion 26c of the second operation wire 26 butts against the inner wall of the tubular organ V2 to be further curved, and spirally expands (see FIG. 18B) and enters between the stone K and the inner wall of the tubular organ V2 to start an operation of enclosing the stone K (see FIG. 24). At this time, the stone K is supported by the plural framework wire members 20, and therefore, the stone K is hardly positionally shifted.

Figure 25:
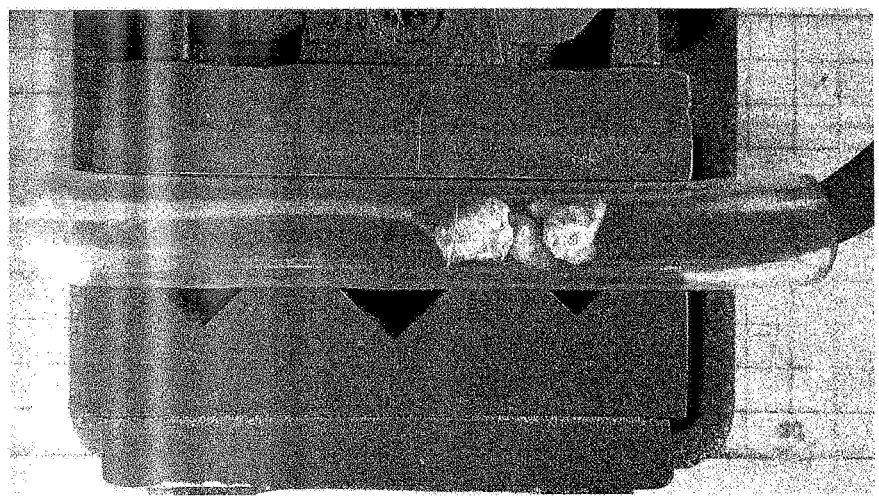
FIG. 25 is a photograph of a third use state of the foreign object capturing device.
Figure 26:
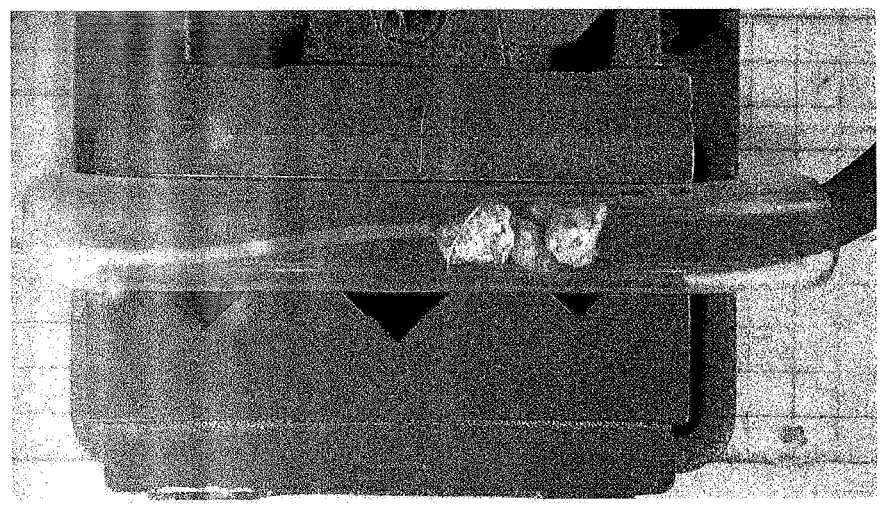
FIG. 26 is a photograph of a fourth use state of the foreign object capturing device.

When the second slider 42 is further slid toward the distal end, the curved portion 26c of the second operation wire 26 is moved toward the distal end so that the loop interval is narrowed (see FIG. 19A), and the stone K is further enclosed (see FIG. 25). When the second slider 42 is further slid toward the distal end, the curved portion 26c of the second operation wire 26 is moved to the distal end side with respect to the bundling member 22, and, as shown in FIGS. 19B, 20, and 26, can enclose and capture the stone K so as to tangle with the stone, and the stone can be taken out in a manner that it is scraped off from the inner wall of the tubular organ V2 (see FIG. 27).

The stone K can be discharged into the tubular organ V1 by, in the above-described state, pulling the whole foreign object capturing device 10a toward the proximal side, moving the plural framework wire members 20 and the second operation wire 26 to the large-diameter tubular organ V1 such as the duodenum, and adequately sliding the first slider 41 and second slider 42 of the operation handle 40. Thereafter, the stones K in the tubular organ V2 can be captured and discharged by repeating the work plural times.

According to the foreign object capturing device 10a in the embodiment, as described above, the second operation wire 26 is caused to have a curved shape as a free-state initial shape as viewed from the axial distal end side. When the second operation wire 26 is moved relative to the first operation wire 15 toward the distal end, therefore, the curved portion expands along the inner wall of a body cavity, enters between a foreign object and the inner wall of the body cavity, and encloses and captures the foreign object, and the foreign object can be taken out in a manner that it is scraped off from the inner wall of the body cavity.

Furthermore, the embodiment is configured so that the second operation wire 26 expands in the outer radial direction by moving the second operation wire 26 relative to the first operation wire 15 toward the distal end, and moves to the distal end side with respect to the coupling portion (bundling member 22) between the distal ends of the plural framework wire members 20 and the distal end of the second operation wire 26 by further relatively moving the second operation wire 26 toward the distal end.

In the case where plural large foreign objects lie in a line along the path in a body cavity as shown in FIG. 20, the foreign objects get stuck unless the foreign objects are sequentially taken out beginning with the front foreign object. In such case, according to the foreign object capturing device 10a of the embodiment, the second operation wire 26 expands in the outer radial direction and moves to the distal end side with respect to the coupling portion (bundling member 22) between the distal ends of the plural framework wire members 20 and the distal end of the second operation wire 26 by placing the distal end portion of the foreign object capturing device 10a in front of the most front foreign object, and moving the second operation wire 26 relative to the first operation wire 15 toward the distal end. Therefore, the second operation wire 26 can tangle with and capture the front foreign object, and the foreign objects can be sequentially taken out beginning with the front foreign object.

Example

Production of Foreign Object Capturing Device

A foreign object capturing device having a structure similar to the foreign object capturing device 10a of the embodiment shown in FIGS. 14 to 20 is produced.

The first operation wire 15 is made of stainless steel, also the plural framework wire members 20 are made of stainless steel, and the second operation wire 26 is formed by a single twisted wire which is configured by twisting 8 wire members made of stainless steel.

(Test for Checking Capture Performance)

Figure 27:
FIG. 27 is a photograph of a fifth use state of the foreign object capturing device.
Figure 28:
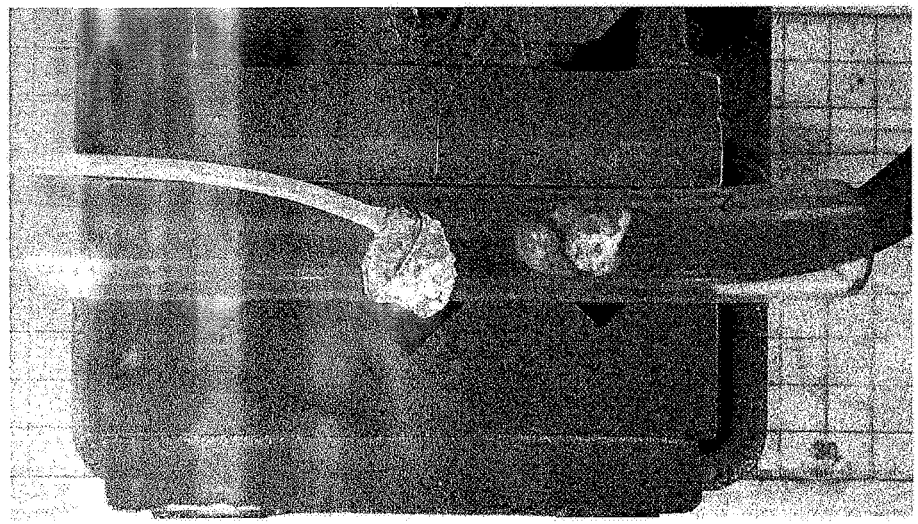
FIG. 28 is a photograph of a sixth use state of the foreign object capturing device.
Figure 29:
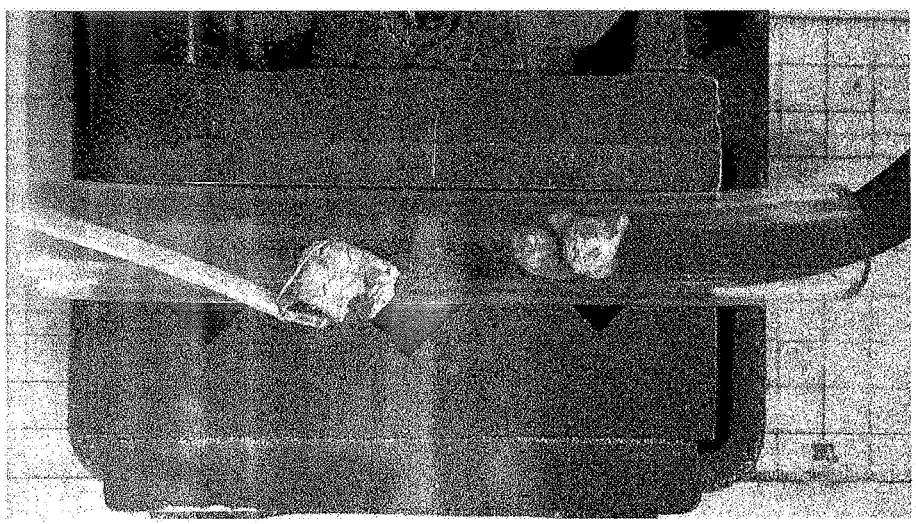
FIG. 29 is a photograph of a seventh use state of the foreign object capturing device.

Plural foreign objects (stones) are placed in a resin tube, and an operation test of capturing the foreign objects is performed using the above-described foreign object capturing device. As described above, as shown in FIGS. 23 to 26, the foreign objects are safely captured by the second operation wire 26, and are taken out as shown in FIG. 27. It is also confirmed that, as shown in FIGS. 28 and 29, the second operation wire 26 can enclose a foreign object so as to tangle with the outer circumference of the foreign object, and capture the foreign object.

REFERENCE SIGNS LIST 10, 10a body-cavity foreign object capturing device (foreign object capturing device)
15 first operation wire
20 framework wire member
25, 26 second operation wire
30 basket
35 resin membrane
40 operation handle
45 catheter

The invention claimed is:

1. A body-cavity foreign object capturing device, including:
   a first operation wire;
   plural framework wire members, base end portions of which are coupled to a distal end portion of the first operation wire, and distal end portions of which are bundled together; and
   a second operation wire which is coupled to the distal end portions of the plural framework wire members, which extend toward a base end of the first operation wire while being separated from the first operation wire, and which is operable independently from the first operation wire, wherein the second operation wire has a curved shape as a free-state initial shape as viewed from an axial distal end side so as to include:
- a distal end portion which is bent in an outer radial direction from a coupling portion with the plural framework wire members;
- a bent portion which extends in a circumferential direction from the distal end portion while expanding; and
- a curved portion which extends from the bent portion and returns toward the base end of the first operation wire while being gently curved.

2. The body-cavity foreign object capturing device of claim 1, wherein the second operation wire is configured to:
- expand in an outer radial direction by moving the second operation wire relative to the first operation wire toward the distal end; and
- move to the distal end side with respect to the coupling portion between the distal ends of the plural framework wire members and the distal end of the second operation wire by relatively moving the second operation wire toward the distal end.

3. The body-cavity foreign object capturing device of claim 1, wherein the framework wire members are configured to expand to form a basket by moving the first operation wire relative to the second operation wire toward the distal end, and a depth of the basket is reduced by relatively moving the first operation wire toward the distal end.

4. The body-cavity foreign object capturing device of claim 3, wherein a resin membrane is disposed in a portion of the basket, and
wherein the portion of the basket ranges from a coupling portion between distal end portions of the plural framework wire members and a distal end portion of the second operation wire, to a portion where a diameter of the basket is maximally expanded.

5. The body-cavity foreign object capturing device of claim 4, wherein the plural framework wire members are placed at predetermined intervals along a circumferential direction thereof in a state where the diameter of the basket is expanded,
wherein the second operation wire is configured by a single wire, and is placed in a position circumferentially opposed to a portion where the plural framework wire members are placed in the state where the diameter of the basket is expanded, and
wherein an interval between the second operation wire and one of the framework wire members which is closest to the second operation wire is wider than intervals among the plural framework wire members.

6. The body-cavity foreign object capturing device of claim 3, wherein the plural framework wire members are placed at predetermined intervals along a circumferential direction thereof in a state where a diameter of the basket is expanded,
wherein the second operation wire is configured by a single wire, and is placed in a position circumferentially opposed to a portion where the plural framework wire members are placed in the state where the diameter of the basket is expanded, and
wherein an interval between the second operation wire and one of the framework wire members which is closest to the second operation wire is wider than intervals among the plural framework wire members.

* * * * *